United States Patent [19]

Yamatsu et al.

[11] Patent Number: 4,482,734

[45] Date of Patent: Nov. 13, 1984

[54] POLYPRENYL COMPOUNDS

[75] Inventors: Isao Yamatsu, Ushikumachi; Takeshi Suzuki, Ushikumachi; Shinya Abe, Kukizakimachi; Yuichi Inai, Tokyo; Yoshikazu Suzuki, Ichinomiya; Osamu Tagaya, Gifu, all of Japan

[73] Assignee: Eisai Co., Ltd., Tokyo, Japan

[21] Appl. No.: 504,769

[22] Filed: Jun. 16, 1983

[30] Foreign Application Priority Data

Jun. 22, 1982 [JP] Japan ................................. 57-106204

[51] Int. Cl.³ ............................................ C07C 69/76
[52] U.S. Cl. ..................................... 560/104; 562/495; 424/308; 424/317
[58] Field of Search ......................... 560/104; 562/495; 424/308, 317

[56] References Cited

U.S. PATENT DOCUMENTS 4,362,891 12/1982 Guerrah et al. ..................... 562/495
4,390,476 6/1983 Märky ................................ 562/495

FOREIGN PATENT DOCUMENTS 1139993 1/1969 United Kingdom ................. 562/498

*Primary Examiner*—Paul J. Killos
*Attorney, Agent, or Firm*—Flynn, Thiel, Boutell & Tanis

[57] ABSTRACT

The polyprenyl compound having the formula:

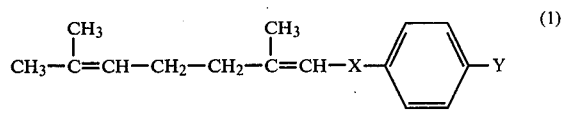

wherein X represents a group of the formula: —CH=CH—, a group of the formula:

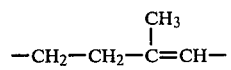

or a group of the formula:

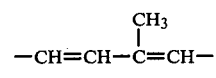

and Y represents a group of the formula: —COOR¹ in which R¹ represents a hydrogen atom or a lower alkyl group or a group of the formula:

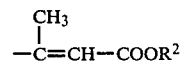

in which R² represents a hydrogen atom or a lower alkyl group, is new and useful as a medicine.

11 Claims, No Drawings

POLYPRENYL COMPOUNDS

The present invention relates to polyprenyl compounds useful as excellent medicines. More particularly, the present invention relates to polyprenyl compounds of the general formula:

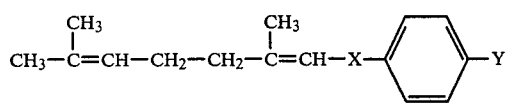

wherein X represents a group of the formula: —CH=CH—, a group of the formula:

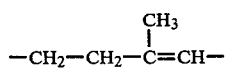

or a group of the formula:

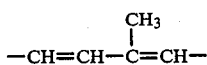

and Y represents a group of the formula: —COOR¹ in which R¹ represents a hydrogen atom or a lower alkyl group or a group of the formula:

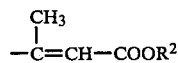

in which R² represents a hydrogen atom or a lower alkyl group,
processes for producing them and medicines containing them.

The lower alkyl groups in the definition of R¹ and R² in the above general formula [I] are straight-chain or branched alkyl groups having 1 to 6 carbon atoms, such as methyl, ethyl, n-propyl, isopropyl, n-butyl, isobutyl, 1-methylpropyl, tert-butyl, n-pentyl, 1-ethylpropyl, isoamyl and n-hexyl groups.

The polyprenyl compounds provided by the present invention are new compounds which have not been mentioned in literature. They have various excellent physiological effects and are highly valuable as medicines.

Namely, the compounds of the present invention are useful for the prevention and treatment of cancer or pre-cancer, dermal diseases accompanied by cornification such as acne and psoriasis, allergic dermal diseases and mucous membrane diseases due to inflammation, degeneration and dysplasia.

The compounds of the present invention having an extremely low toxicity and a high safety can be administered continuously for a long time.

Examples of typical compounds of the present invention will be shown below. As a matter of course, these compounds by no means limit the invention.

3-[4-(4,8-Dimethyl-1,3,7-nonatrienyl)phenyl]-2-butenoic acid,
Ethyl p-(2,6,10-trimethyl-1,5,9-undecatrienyl)-benzoate,
p-(2,6,10-Trimethyl-1,5,9-undecatrienyl)benzoic acid,
Methyl p-(2,6,10-trimethyl-1,5,9-undecatrienyl)-benzoate,
Ethyl p-(2,6,10-trimethyl-1,3,5,9-undecatetraenyl)-benzoate,
p-(2,6,10-Trimethyl-1,3,5,9-undecatetraenyl)benzoic acid,
Methyl p-(2,6,10-trimethyl-1,3,5,9-undecatetraenyl)-benzoate,
Butyl p-(2,6,10-trimethyl-1,3,5,9-undecatetraenyl)-benzoate,
Ethyl 3-[4-(4,8-dimethyl-1,3,7-nonatrienyl)phenyl]-2-butenoate,
Methyl 3-[4-(4,8-dimethyl-1,3,7-nonatrienyl)phenyl]-2-butenoate,
Propyl 3-[4-(4,8-dimethyl-1,3,7-nonatrienyl)phenyl]-2-butenoate,
Pentyl 3-[4-(4,8-dimethyl-1,3,7-nonatrienyl)phenyl]-2-butenoate,
Propyl p-(2,6,10-trimethyl-1,5,9-undecatrienyl)-benzoate, and
Propyl p-(2,6,10-trimethyl-1,3,5,9-undecatetraenyl)-benzoate.

The compounds [I] of the present invention may be produced by various processes. Some examples of the generally employed processes will be shown below:

Process A:
When X in the general formula [I] represents a group of the formula: —CH=CH—, a group of the formula:

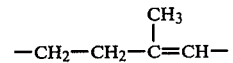

or a group of the formula:

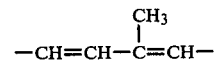

and Y represents a group of the formula —COOH or a group of the formula:

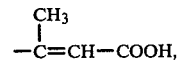

a corresponding ester is hydrolyzed in the presence of an alkali such as KOH or NaOH to obtain an intended product as shown by the following reaction scheme:

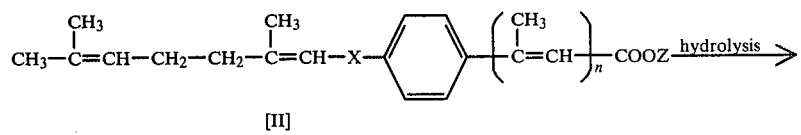

[II]

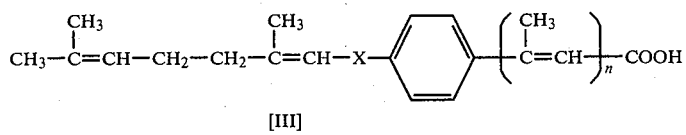

[III]

wherein X has the same meaning as above, Z represents a lower alkyl group and n represents 0 or 1.

Process B:

When X in the general formula [I] represents a group of the formula:

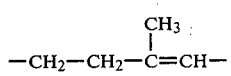

and Y represents a group of the formula: —COOR$^1$ or a group of the formula:

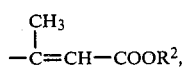

in which R$^1$ and R$^2$ each represent a lower alkyl group, an intended compound is produced according to, for example, the following reaction scheme:

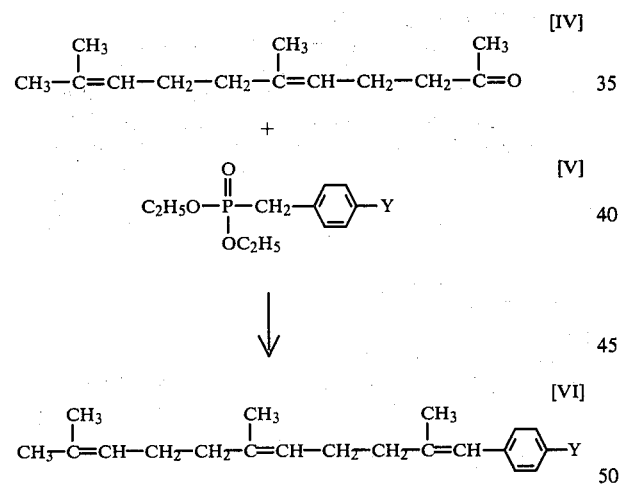

Process C:

When X in the general formula [I] represents a group of the formula:

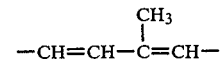

and Y represents a group of the formula: —COOR$^1$ or a group of the formula:

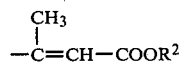

in which R$^1$ and R$^2$ each represent a lower alkyl group, an intended compound is produced according to, for example, the following reaction scheme:

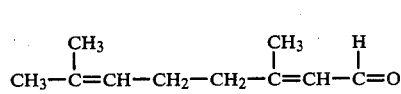

Process D:

When X in the general formula [I] represents a group of the formula: —CH=CH— and Y represents a group of the formula:

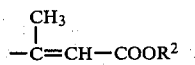

in which R$^2$ represents a lower alkyl group, an intended compound is produced by a reaction according to, for example, the following reaction scheme:

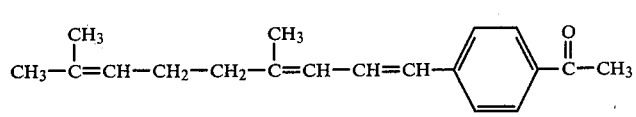

+

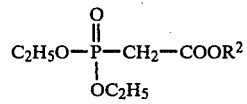

[XI]

↓

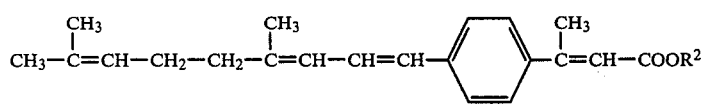

[XII]

Excellent pharmacological effects of the compounds of the present invention will be shown below with reference to the effects of some typical compounds:

Experiments:

(1) Methods of experiments:

After shaving on the back neck (5 cm$^2$) of 60 day-old female ICR mice, a 75 mg/100 ml solution of 7,12-dimethylbenzo-[2]-anthracene in acetone was applied to the 60 day-old and 75 day-old mice in an amount of 0.2 ml/mouse. A 250 mg/100 ml solution of croton oil in acetone was applied to the mice in an amount of 0.2 ml/mouse twice a week until the initiation of the therapeutic experiments. After 3 to 7 papillomata each having a 30 to 60 mm diameter had appeared in each mouse, the therapeutic experiments were begun.

The following test compound was dissolved in peanut oil to obtain a 20 mg/ml solution. The solution was administered to the mice orally. Vitamin A was incorporated in a food for the mice in an amount of 2,500 I.U./kg food. The compound in an amount shown in the following table was administered 10 times (once a day) in 14 days. On the 7th and 14th days, the diameters of the papillomata were measured and the total diameter in each mouse was determined. The total diameter after the treatment was compared with that determined prior to the treatment to obtain a papilloma-controlling rate.

(2) Test compounds:

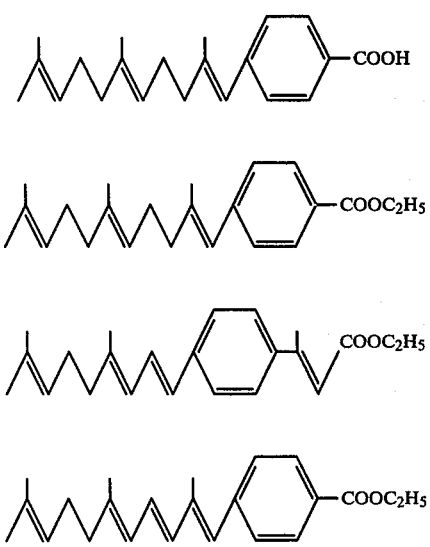

Compound A

Compound B

Compound C

Compound D (3) Experimental results:
The results are shown in Table 1.

TABLE 1

| Compound | Dose | Papilloma-controlling rate 7th day | 14th day |
|---|---|---|---|
| Control (Peanut oil alone) | | +7.3 | +5.9 |
| Compound A | 40 mg/kg P.O. — | −47.6 | −84.0 |
| | 8 mg/kg P.O. | −10.4 | −26.5 |
| Compound B | 40 mg/kg P.O. | −39.6 | −60.0 |
| | 20 mg/kg P.O. | −19.4 | −35.9 |
| | 10 mg/kg P.O. | −14.1 | −29.8 |
| Compound C | 20 mg/kg P.O. | −21.8 | −32.7 |
| Compound D | 20 mg/kg P.O. | −47.3 | −74.4 |
| | 10 mg/kg P.O. | −50.2 | −70.7 |
| | 5.0 mg/kg P.O. | −43.4 | −65.4 |
| | 2.5 mg/kg | −36.2 | −60.5 |

It is apparent from these pharmacological results that the compounds of the present invention have excellent effects of controlling papillomata and, therefore, they are useful as a prophylactic/therapeutic agent for cancer or pre-cancer. Further, they are useful for the prevention and treatment of dermal diseases accompanied by cornification such as acne, disease of pilosebaceous system, ichthyosis and psoriasis, inflammatory, non-inflammatory or allergic dermal diseases and mucous membrane diseases due to inflammation, degeneration and dysplasia.

The dermal diseases accompanied by cornification are those accompanied by hyperkeratosis, parakeratosis or dyskeratosis. As particular examples of the diseases, there may be mentioned psoriasis, acne, acne vulgaris, Darier's disease, palmoplantar pustulosis, lichen planus, ichthyosis, erythroderma, pityriasis rubra pilasis, ketatosis senilis, keratosis palmaris et plantaris and skin tumors.

The compounds of the present invention having an extremely low toxicity are usable continuously over a long time and highly valuable as carcinostatic agents and also as prophylactic/therapeutic agents for dermal diseases accompanied by cornification. Particularly, the compounds of the present invention are most suitable for the prevention and treatment of the dermal diseases accompanied by cornification, since they are quite safe, while external steroidal drugs used heretofore as remedies for the dermal diseases accompanied by cornification are unsuitable for use in large amounts continuously over a long time because of their strong adverse reactions.

In the administration of the compounds of the present invention as carcinostatic agents or prophylactic/therapeutic agents for the dermal diseases accompanied by cornification, they may be administered either orally in the form of powders, granules, capsules or syrups or non-orally in the form of suppositories, injections or external medicines. The dosage which varies considerably depending on the condition of the disease and the age of the patient is generally about 5 to 1,000 mg per day for adults.

In manufacturing medicinal preparations from the compounds of the present invention, the compounds are shaped into tablets, granules, powders, capsules, injections or suppositories by conventional methods generally employed in this technical field.

More particularly, in manufacturing an oral solid preparation, an excipient and, if necessary, a binder, disintegrator, lubricant, colorant, corrigent, etc. are added to the main ingredients and the resulting mixture is shaped into tablets, coated tablets, granules, powders or capsules by ordinary methods.

As the excipients, there may be used, for example, lactose, corn starch, white sugar, glucose, sorbital, crystalline cellulose and silicon dioxide. As the binders, there may be used, for example, polyvinyl alcohol, polyvinyl ether, ethylcellulose, methylcellulose, acacia, tragacanth, gelatine, shellac, hydroxypropylcellulose, hydroxypropylstarch and polyvinylpyrrolidone. As the disintegrators, there may be used, for example, starch, agar, gelatin powder, crystalline cellulose, calcium carbonate, sodium hydrogencarbonate, calcium citrate, dextrin and pectin. As the lubricants, there may be used, for example, magnesium stearate, talc, polyethylene glycol, silica and hardened vegetable oils. As the colorants, there may be used those acceptable for use as additives for medicines. As the corrigents, there may be used, for example, cocoa powder, menthol, aromatic powder, peppermint oil, borneol and cinnamon powder. These tablets and granules may be coated with sugar, gelatin, etc., if necessary.

In manufacturing injections, a pH regulator, buffering agent, stabilizer, preservative, solubilizer and suspending agent are added, if necessary, to the main ingredients and then subcutaneous, intramuscular or intravenous injections are prepared from the mixture by conventional methods.

The following examples will further illustrate the present invention, which by no means limit the invention.

EXAMPLE 1

3-[4-(4,8-Dimethyl-1,3,7-nonatrienyl)phenyl]-2-butenoic acid 5.4 g of potassium hydroxide was dissolved in 100 ml of isopropanol. 14 g of ethyl 3-[4-(4,8-dimethyl-1,3,7-nonatrienyl)phenyl]-2-butenoate was added to the solution under heating, reflux and stirring. After 30 min, the resulting solution was poured into ice/water and extracted with 100 ml of n-hexane. The aqueous layer was made acidic with dilute hydrochloric acid, extracted with ethyl ether and washed with water. After drying over magnesium sulfate, the product was concentrated and the resulting concentrate was crystallized from n-hexane to obtain 8 g of intended 3-[4-(4,8-dimethyl-1,3,7-nonatrienyl)phenyl]-2-butenoic acid as light yellow crystals.

Melting point: 102.5°–103.5° C.

Elementary analysis as $C_{21}H_{26}O_2$:

| | C | H |
|---|---|---|
| Calculated (%) | 81.25 | 8.44 |
| Found (%) | 81.23 | 8.51 |

NMR(CDCl$_3$) δ:1.63(3H, s), 1.70(3H, s), 1.89(3H, s), 2.1~2.2(4H), 2.60(3H, s), 5.11(1H, broad), 6.04(1H, d, J = 11), 6.20 (1H, s), 6.44(1H, d, J = 15), 7.08(1H, dd, J = 15.11), 7.44(4H, s), 10.2(1H, broad)

EXAMPLE 2

Ethyl p-(2,6,10-trimethyl-1,5,9-undecatrienyl)benzoate 10 g of geranylacetone was added to a solution of 24 g of ethyl 4-[(diethoxyphosphinyl)methylbenzoate and 5.2 g of sodium ethylate in 50 ml of dimethylformaldehyde under stirring at room temperature. After one hour, water was added thereto and the mixture was extracted with n-hexane, washed with water, dried over magnesium sulfate and concentrated. The concentrate was purified by means of silica gel column chromatography to obtain 14 g of intended ethyl p-(2,6,10-trimethyl-1,5,9-undecatrienyl)benzoate as a colorless oil.

Elementary analysis as $C_{23}H_{32}O_2$:

| | C | H |
|---|---|---|
| Calculated (%) | 81.13 | 9.47 |
| Found (%) | 81.11 | 9.56 |

MASS (m/e) 340 (M$^+$)
NMR (CDCl$_3$) δ:1.38(3H, J = 7), 1.59 (3H, s), 1.63(3H, s), 1.66(3H, s), 1.88 (3H, s), 1.9~2.3(8H), 4.36(2H, q, J = 7), 5.1(2H, broad), 6.28(1H, s), 7.27(2H, d, J = 8), 7.98(2H, d, J = 8)

EXAMPLE 3 p-(2,6,10-Trimethyl-1,5,9-undecatrienyl)benzoic acid 20 g of potassium hydroxide was dissolved in 200 ml of isopropanol. 50 g of ethyl p-(2,6,10-trimethyl-1,5,9-undecatrienyl)benzoate was added to the solution under heating, reflux and stirring. After 10 min, the solution was poured into ice/water and extracted with 200 ml of n-hexane. The aqueous layer was made acidic with dilute hydrochloric acid, extracted with ethyl ether, washed with water and dried over magnesium sulfate. The product was concentrated to obtain 42 g of crude crystals. The crude crystals were recrystallized from 150 ml of n-hexane to obtain 32 g of intended p-(2,6,10-trimethyl-1,5,9-undecatrienyl)benzoic acid as white crystals.

Melting point: 92°–92.5° C.

Elementary analysis as $C_{21}H_{28}O_2$:

| | C | H |
|---|---|---|
| Calculated (%) | 80.73 | 9.03 |
| Found (%) | 80.56 | 9.18 |

MASS (m/e) 312 (M$^+$)
NMR (CDCl$_3$) δ:1.60(3H, s), 1.64(3H, s), 1.66(3H, s), 1.90 (3H, d, J = 1), 1.95~2.3 (8H), 5.15(2H, broad), 6.31(1H, s), 7.32 (2H, d, J = 8), 8.06(2H, d, J = 8), 11.10(1H, broad)

EXAMPLE 4

Ethyl p-(2,6,10-trimethyl-1,3,5,9-undecatetraenyl)-benzoate

A solution of 50 g of 1-(p-ethoxycarbonyl)-2-methyl-3-(diethoxyphosphinyl)propene and 20 g of citral in 150 ml of dimethylformamide was cooled to −60° C. and stirred. A solution of 8.9 g of sodium ethylate in 150 ml of dimethylformamide was added dropwise thereto over 30 min. After completion of the addition, the stirring was continued at −60° C. for 1 h and the temperature of the reaction liquid was elevated to room temperature. Water was added thereto and the mixture was extracted with n-hexane, washed with water, dried over magnesium sulfate and concentrated. The concentrate was purified by means of silica gel column chromatography to obtain 21 g of an oily product. The product was dissolved in acetone and crystallized at −60° C. to obtain 5.6 g of ethyl 2-(2,6,10-trimethyl-1,3,5,9-undecatetraenyl)benzoate as light yellow crystals.

Melting point: 47°–48° C.

Elementary analysis as $C_{23}H_{30}O_2$:

|  | C | H |
|---|---|---|
| Calculated (%) | 81.61 | 8.93 |
| Found (%) | 81.80 | 8.95 |

MASS (m/e) 338 (M+)

NMR (CDCl$_3$) δ:1.39(3H, d, J = 7), 1.63 (3H, s), 1.69(3H, s), 1.84(3H, d, J = 1), 2.08(3H, d, J = 1), 2.1~2.2(4 H), 4.37(2H, d, J = 7), 5.12(1H, broad), 5.97(1H, d, J = 10), 6.32(1H, d, J = 15), 6.51(1H, bs), 6.63(1H, dd, J = 15.10), 7.35(2H, d, J = 8), 8.00(2H, d, J = 8)

EXAMPLE 5

Ethyl 3-[4-(4,8-dimethyl-1,3,7-nonatrienyl)phenyl]-2-butenoate 8 g of p-(4,8-dimethyl-1,3,7-nonatrienyl)acetophenone was added to a solution of 15 g of triethyl phosphonoacetate and 4.2 g of sodium ethylate in 50 ml of dimethylformaldehyde under stirring at room temperature. After stirring at 70° C. for 3 h, the reaction liquid was poured into ice/water, extracted with n-hexane, washed with water and dried over magnesium sulfate. After concentration followed by silica gel column chromatography, 6.1 g of intended ethyl 3-[4-(4,8-dimethyl-1,3,7-nonatrienyl)-phenyl]-2-butenoate was obtained as light yellow crystals.

Melting point: 32°–32.5° C.

Elementary analysis as $C_{23}H_{30}O_2$:

|  | C | H |
|---|---|---|
| Calculated (%) | 81.61 | 8.93 |
| Found (%) | 81.90 | 8.78 |

MASS (m/e) 338 (M+)

NMR (CDCl$_3$) δ:1.31(3H, s, J = 7), 1.62 (3H, s), 1.69 (3H, s), 1.88 (3H, d, J = 1), 2.1~2.2(4H), 2.57(3H, d, J = 1), 4.22(2H, d, J = 7), 5.12(1H, broad), 6.02(1H, d, J = 11), 6.16(1H, q, J = 1), 6.43(1H, d, J = 15), 7.06 (1H, dd, J = 15,11), 7.41(4H, s)

EXAMPLE OF MANUFACTURE OF PREPARATIONS

Tablets

| | |
|---|---|
| 3-[4-(4,8-dimethyl-1,3,7-nonatrienyl)phenyl]-2-butenoic acid | 10 g |
| anhydrous silicic acid | 50 g |
| crystalline cellulose | 70 g |
| corn starch | 36 g |
| hydroxypropyl cellulose | 10 g |
| magnesium stearate | 4 g |

Tablets each weighing 180 mg were prepared according to the above recipe by conventional methods.

The embodiments of the invention in which an exclusive property or privilege is claimed are defined as follows:

1. Polyprenyl compounds of the general formula:

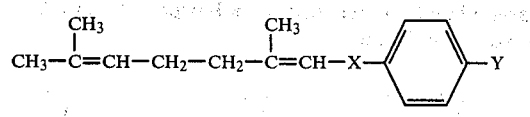

wherein X represents a group of the formula: —CH=CH—, a group of the formula:

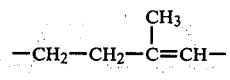

or a group of the formula:

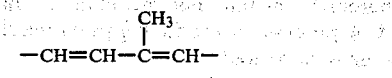

and Y represents a group of the formula: —COOR$^1$ in which R$^1$ represents a hydrogen atom or a lower alkyl group or a group of the formula:

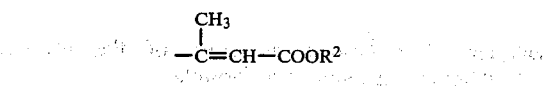

in which R$^2$ represents a hydrogen atom or a lower alkyl group.

2. A polyprenyl compound according to claim 1 which is 3-[4-(4,8-dimethyl-1,3,7-nonatrienyl)phenyl]-2-butenoic acid.

3. A polyprenyl compound according to claim 1 which is ethyl p(2,6,10-trimethyl-1,5,9-undecatrienyl)-benzoate.

4. A polyprenyl compound according to claim 1 which is p-(2,6,10-trimethyl-1,5,9-undecatrienyl)benzoic acid.

5. A polyprenyl compound according to claim 1 which is ethyl p-(2,6,10-trimethyl-1,3,5,9-undecatetraenyl)-benzoate.

6. A polyprenyl compound according to claim 1 which is ethyl 3-[4-(4,8-dimethyl-1,3,7-nonatrienyl)-phenyl]-2-butenoate.

7. A process for producing polyprenyl compounds of the general formula:

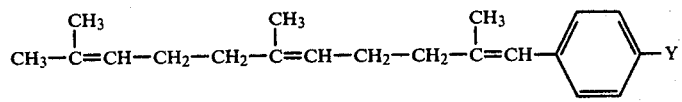

wherein Y represents a group of the formula: —COOR¹ or a group of the formula:

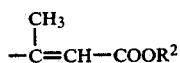

in which R¹ and R² each represents a lower alkyl group, characterized by reacting a polyprenyl ketone compound of the formula:

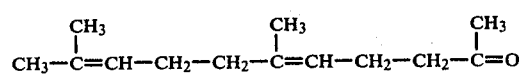

with a compound of the general formula:

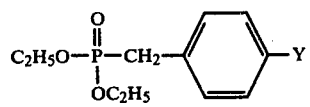

wherein Y has the same meaning as above.

8. A process for producing polyprenyl compounds of the general formula:

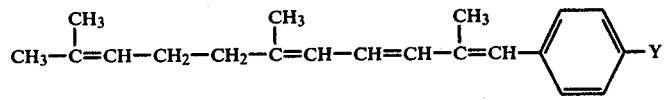

wherein Y represents a group of the formula: —COOR¹ or a group of the formula:

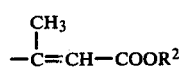

in which R¹ and R² each represent a lower alkyl group, characterized by reacting a polyprenyl ketone compound of the formula:

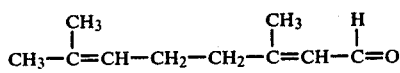

with a compound of the general formula:

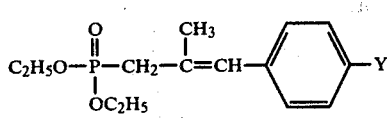

wherein Y has the same meaning as above.

9. A process for producing polyprenyl compounds of the general formula:

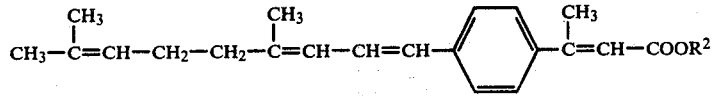

wherein R² represents a lower alkyl group, characterized by reacting a polyprenyl ketone compound of the formula:

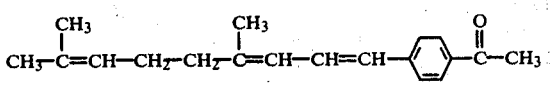

with a compound of the general formula:

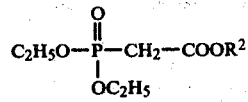

wherein R² has the same meaning as above.

10. A prophylactic/therapeutic agent for cancer or pre-cancer which contains as an active ingredient a polyprenyl compound of the general formula:

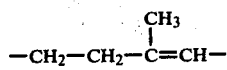

wherein X represents a group of the formula: —CH=CH—, a group of the formula:

$$-CH_2-CH_2-\underset{\underset{CH_3}{|}}{C}=CH-$$

or a group of the formula:

$$-CH=CH-\underset{\underset{CH_3}{|}}{C}=CH-,$$

Y represents a group of the formula: —COOR¹ in which R¹ represents a hydrogen atom or a lower alkyl group or a group of the formula:

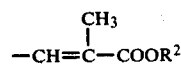

in which R² represents a hydrogen atom or a lower alkyl group.

11. A prophylactic/therapeutic agent for dermal diseases accompanied by cornification which contains as an active ingredient a polyprenyl compound of the general formula:

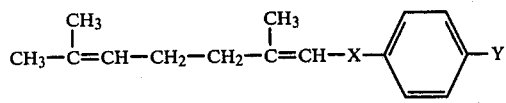

wherein X represents a group of the formula: —CH=CH—, a group of the formula:

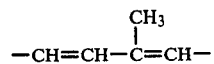

or a group of the formula:

$$-CH=CH-\underset{\underset{CH_3}{|}}{C}=CH-$$

and Y represents a group of the formula: —COOR¹ in which R¹ represents a hydrogen atom or a lower alkyl group or a group of the formula:

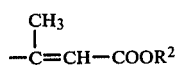

in which R² represents a hydrogen atom or a lower alkyl group.

* * * * *